United States Patent [19]

Burdette et al.

[11] Patent Number: 5,733,315
[45] Date of Patent: Mar. 31, 1998

[54] METHOD OF MANUFACTURE OF A TRANSURETHRAL ULTRASOUND APPLICATOR FOR PROSTATE GLAND THERMAL THERAPY

[76] Inventors: Everette C. Burdette, 2115 Seaton Ct., Champaign, Ill. 61821; Chris J. Diederich, 19 Nova La., Novato, Calif. 94945

[21] Appl. No.: 332,997

[22] Filed: Nov. 1, 1994

Related U.S. Application Data

[63] Continuation-in-part of Ser. No. 333,005, Aug. 17, 1994, which is a continuation-in-part of Ser. No. 83,967, Jun. 25, 1993, Pat. No. 5,391,197, which is a continuation-in-part of Ser. No. 976,232, Nov. 13, 1992, abandoned.

[51] Int. Cl.[6] .................................................. A61N 7/02
[52] U.S. Cl. ........................... 607/97; 128/662.03; 601/3
[58] Field of Search ..................... 128/662.03, 662.06; 601/2, 3; 607/96, 97, 104, 154, 155, 156; 604/22

[56] References Cited

U.S. PATENT DOCUMENTS

| Re. 33,791 | 1/1992 | Carr . | |
|---|---|---|---|
| 3,977,408 | 8/1976 | MacKew . | |
| 4,311,154 | 1/1982 | Sterzer et al. . | |
| 4,378,806 | 4/1983 | Henley-Cohn . | |
| 4,462,408 | 7/1984 | Silverstein et al. | 128/662.06 |
| 4,586,512 | 5/1986 | Do-huu et al. | 128/662.03 |
| 4,601,296 | 7/1986 | Yerushalmi . | |
| 4,612,940 | 9/1986 | Kasevich et al. . | |
| 4,662,383 | 5/1987 | Sogawa et al. . | |
| 4,671,293 | 6/1987 | Shaulov | 128/662.03 |
| 4,681,122 | 7/1987 | Winters et al. . | |
| 4,813,429 | 3/1989 | Eshel et al. . | |
| 4,955,377 | 9/1990 | Lennox et al. . | |
| 4,967,765 | 11/1990 | Turner et al. . | |
| 5,002,058 | 3/1991 | Martinelli | 128/662.06 |
| 5,007,437 | 4/1991 | Sterzer . | |
| 5,025,778 | 6/1991 | Silverstein et al. . | |
| 5,070,879 | 12/1991 | Herres | 128/662.06 |
| 5,090,414 | 2/1992 | Takano . | |
| 5,158,536 | 10/1992 | Sekins et al. . | |
| 5,167,231 | 12/1992 | Matsui | 128/662.03 |
| 5,271,408 | 12/1993 | Breyer et al. | 128/692 |
| 5,344,435 | 9/1994 | Turner et al. | 607/156 |
| 5,351,691 | 10/1994 | Brommersma | 128/662.03 |
| 5,526,815 | 6/1996 | Granz et al. | 607/97 |

FOREIGN PATENT DOCUMENTS

| 0 370 890 A1 | 11/1989 | European Pat. Off. . | |
| 468-847 | 1/1992 | European Pat. Off. | 601/3 |
| 28 16 391 A1 | 11/1978 | Germany . | |
| 24 07 599 C3 | 1/1982 | Germany . | |
| 2 045 620 A | 3/1980 | United Kingdom . | |
| 93/16641 | 9/1993 | WIPO | 128/662.03 |

OTHER PUBLICATIONS

"Prostatic and Periprostatic Interstital Temperature Measurements in Patients Treated with Transrectal Thermal Therapy (Local Intracavitary Microwave Hyperthermia)," Steven A. Kaplan et al., The Journal of Urology, vol. 147, pp. 1562–1565 (Jun. 1992).

(List continued on next page.)

Primary Examiner—Jennifer Bahr
Assistant Examiner—Eric F. Winakur
Attorney, Agent, or Firm—Reinhart, Boerner, Van Deuren, Norris & Rieselbach, s.c.

[57] ABSTRACT

An apparatus for applying thermal therapy to a prostate gland, comprising a support tube having a longitudinal central passageway, a power lead channeled through the longitudinal central passageway and an ultrasound crystal disposed around at least part of the support tube. The ultrasound crystal is coupled to the power lead which provides the power to energize the ultrasound crystal and generate ultrasound energy providing thermal therapy to the prostate gland. The ultrasound crystal further includes inactivated portions for reducing ultrasound energy directed to the rectal wall of the patient. A sealant is disposed in contact with the ultrasound crystal allowing vibration necessary for efficient ultrasound energy radiation for the thermal therapy to the prostate gland.

3 Claims, 14 Drawing Sheets

OTHER PUBLICATIONS

"Parameters Predictive for Complications of Treatment with Combined Hyperthermia and Radiation Therapy," Daniel S. Kapp et al., I.J. of Radiation Oncology, Biology, Physics, vol. 22(5), pp. 999–1008.

"Introduction to hyperthermia device evaluation,", M.D. Sapozink et al., Int. J. Hyperthermia, vol. 4(1), pp. 1–15 (1988).

"Stanford University institutional report. Phase I evaluation of equipment for hyperthermia treatment of cancer," Daniel S. Kapp et al., Int. J. Hyperthermia, vol. 4(1), pp. 75–115 (1988).

"Clinical evaluation of hyperthermia equipment: The University of Arizona Institutional Report for the NCI Hyperthermia Equipment Evaluation Contract," David S. Shimm et al., Int. J. Hyperthermia, vol. 4(1), pp. 39–51 (1988).

"High–Frequency Transmitter for the Localized Heat Treatment of the Prostate Gland," Otto Petrowicz et al., National Cancer Institute Monograph No. 61, pp. 473–476 (1982).

"Microwave Surgical Treatment of Diseases of Prostate," Harada et al., Urology, Dec. 1985, vol XXVI, No. 6.

"Design and Thermometry of an Intracavitary Microwave Applicator Suitable For Treatment of Some Vaginal and Rectal Cancers," Ding–Jui Li, M.D. et al., Int. J. Radiation Oncology Biol. Phys., vol. 10, No. 11, pp. 2155–2162, Nov. 1984.

"Cancer Therapy by Hyperthermia and Radiation," edited by C. Streffer et al., proceedings of the 2nd International Symposium, Essen, Jun. 2–4, 1977.

"Induction of Hyperthermia in Deep–Seated Tumors by a Special Microwave Applicator," J. Mendecki et al., proceedings of the 2nd International Symposium, Essen, Jun. 2–4, 1977.

"An Interstitial Device for Microwave Hyperthermia of Human Tumors," LeBourgeois et al., proceedings of the 2nd International Symposium, Essen, Jun. 2–4, 1977.

METHOD OF MANUFACTURE OF A TRANSURETHRAL ULTRASOUND APPLICATOR FOR PROSTATE GLAND THERMAL THERAPY

The present application is a continuation-in-part of a simultaneously filed U.S. patent application Ser. No. 08/333,005, filed Aug. 17, 1994 entitled Transurethral Ultrasound Applicator for Prostate Gland Thermal Therapy, which is a continuation-in-part of U.S. patent application Ser. No. 08/083,967, filed Jun. 25, 1993, now U.S. Pat. No. 5,391,197, which is a continuation-in-part of U.S. patent application Ser. No. 07/976,232, filed Nov. 13, 1992, now abandoned in favor of U.S. patent application Ser. No. 08/291,336, now abandoned. The Detailed Description of the Preferred Embodiment of U.S. patent application Ser. No. 08/083,967 is incorporated herein for additional details regarding example delivery systems and ultrasound energy deposition techniques.

The present invention relates generally to an apparatus and method for performing a thermotherapy patient treatment protocol. More particularly, the invention relates to a novel apparatus and method for heating the prostate gland for therapeutic purposes.

Thermotherapy treatment is a relatively new method of treating diseased and/or undesirably enlarged human prostate tissues. Hyperthermia treatment is well known in the art, involving the maintaining of a temperature between about 41.5° through 45° C. Thermotherapy, on the other hand, usually requires energy application to achieve a temperature above 45° C. for the purposes of coagulating the target tissue. Tissue coagulation beneficially changes the density of the tissue. As the tissue shrinks, forms scars and is reabsorbed, the impingement of the enlarged tissues, such as an abnormal prostate, is substantially lessened.

The higher temperatures required by thermotherapy require delivery of larger amounts of energy to the target prostate tissues. At the same time, it is important to shield nontarget tissues from the high thermotherapy temperatures used in the treatment. Providing safe and effective thermotherapy, therefore, requires devices which have further capabilities compared to those which are suitable for hyperthermia.

Though devices and methods for treating benign prostatic hyperplasia have evolved dramatically in recent years, significant improvements have not occurred and such progress is badly needed. As recently as 1983, medical textbooks recommended surgery for removing impinging prostatic tissues and four different surgical techniques were utilized. Suprapubic prostatectomy was a recommended method of removing the prostate tissue through an abdominal wound. Significant blood loss and the concomitant hazards of any major surgical procedure were possible with this approach.

Perineal prostatectomy was an alternatively recommended surgical procedure which involved gland removal through an incision in the perineum. Infection, incontinence, impotence or rectal injury were more likely with this method than with alternative surgical procedures.

Transurethral resection of the prostate gland has been another recommended method of treating benign prostatic hyperplasia. This method required inserting a rigid tube into the urethra. A loop of wire connected with electrical current was rotated in the tube to remove shavings of the prostate at the bladder orifice. In this way, no incision was needed. However, strictures were more frequent and repeat operations were sometimes necessary.

The other recommended surgical technique for treatment of benign prostatic hyperplasia was retropubic prostatectomy. This required a lower abdominal incision through which the prostate gland was removed. Blood loss was more easily controlled with this method, but inflammation of the pubic bone was more likely.

With the above surgical techniques, the medical textbooks noted the vascularity of the hyperplastic prostate gland and the corresponding dangers of substantial blood loss and shock. Careful medical attention was necessary following these medical procedures.

The problems previously described led medical researchers to develop alternative methods for treating benign prostatic hyperplasia. Researchers began to incorporate heat sources in Foley catheters after discovering that enlarged mammalian tissues responded favorably to increased temperatures. Examples of devices directed to treatment of prostate tissue include U.S. Pat. No. 4,662,383 (Harada), U.S. Pat. No. 4,967,765 (Turner), U.S. Pat. No. 4,662,383 (Sogawa) and German Patent No. DE 2407559 C3 (Dreyer). Though these references disclosed structures which embodied improvements over the surgical techniques, significant problems still remained unsolved.

Recent research has indicated that enlarged prostate glands are most effectively treated with higher temperatures than previously thought. Complete utilization of this discovery has been tempered by difficulties in shielding rectal wall tissues and other nontarget tissues. While shielding has been addressed in some hyperthermia prior art devices, the higher energy field intensities associated with thermotherapy necessitate structures having further capabilities beyond those suitable for hyperthermia. For example, the symmetrical microwave-based devices disclosed in the above-referenced patents have generally produced relatively uniform cylindrical energy fields. Even at the lower energy field intensities encountered in hyperthermia treatment, unacceptably high rectal wall temperatures have limited treatment periods and effectiveness. Further, while shielding using radioreflective fluid has been disclosed in the prior art (see for example European Patent Application No. 89,403,199) the location of such radioreflective fluid appears to increase energy field intensity at the bladder and rectal wall. This is contrary to one of the objects of the present invention.

In addition, efficient and selective cooling of the devices is rarely provided. This increases patient discomfort and increases the likelihood of healthy tissue damage. These problems have necessitated complex and expensive temperature monitoring systems along the urethral wall.

Finally, the symmetrical designs of the above-referenced devices do not allow matching of the energy field to the shape of the abnormally enlarged prostate gland. Ideally, the energy field reaching the tissues should be asymmetric and generally should expose the upper and lateral (side) impinging lobes of the prostate gland to the highest energy. In addition, the field is ideally substantially elliptical such that the energy reaching the sphincters is minimized.

It is therefore an object of the invention to provide an improved apparatus and method suitable for ultrasound treatment of tissue.

It is a further object of the invention to provide an improved apparatus and method for thermotherapy treatment which provides a smaller probe with higher ultrasound energy output on target tissues.

It is yet a further object of the invention to provide a novel method and apparatus having high ultrasound energy output on target tissues while producing substantially no energy output directed to nontarget tissues.

It is yet another object of the invention to provide an improved applicator designed to be inserted into an orifice of a male patient, wherein the applicator includes a small diameter ultrasound probe.

It is a still further object of the invention to provide a novel means for dynamic monitoring of the treatment temperature distribution and to use such information to aid in the control of the deposited power level and its distribution.

It is another object of the invention to provide an improved ultrasonic applicator which can be inserted into the urethra and can be positioned with respect to the prostate and maintained in position during treatment.

It is a further object of the invention to provide an improved method and apparatus using ultrasound energy for the treatment of prostate disease and, more particularly to provide an ultrasound applicator consisting of multiple transducers which can be inserted into the urethra or rectum and direct the energy in such a manner as to selectively treat the prostate gland.

It is yet another object of the invention to provide a novel method and apparatus utilizing ultrasound energy to achieve therapeutic temperatures in the prostate with better control of power deposition spatially within the prostate gland than is possible with prior art devices.

It is an additional object of the invention to provide an array of ultrasound transducers producing an energy field having a gap or "dead zone" whereby tissues (such as the rectum, the distal sphinchter and the verumontanum) are protected from energy transmission.

It is a further object of the invention to provide improved control of both the ultrasonic power level and the distribution of the power deposited in the prostate in a dynamic fashion which compensates for physiological changes (temperature, blood flow effects) that can occur during therapy and accommodates operator-desired alterations in the therapeutic energy distribution within the prostate.

It is another object of the invention to provide an improved thermotherapy device which includes a collimated irradiation of a target zone generally and selective cooling of nontarget tissues.

It is still an additional object of the invention to provide an improved thermotherapy device which reduces tissue damage and discomfort by providing more effective cooling to nontarget tissues.

It is an additional object of the invention to provide an improved thermotherapy apparatus having one or more extended, and nondistensible but expandable balloons.

It is an additional object of the invention to provide an improved thermotherapy device which includes ultrasound transducers or other energy sources capable of producing a substantially asymmetric energy output field, thus minimizing energy reaching the rectal wall in benign pro static hyperplasia thermotherapy treatment.

It is still a further object of the invention to provide an improved thermotherapy apparatus which produces an energy field shaped in accordance with the enlarged mammalian gland to be treated.

Other advantages and features of the invention, together with the organization and manner of operation thereof, will become apparent from the following detailed description when taken in conjunction with the accompanying drawings, wherein like elements have like numerals throughout the drawings.

DETAILED DESCRIPTIONS OF PREFERRED EMBODIMENT

Figure 1:
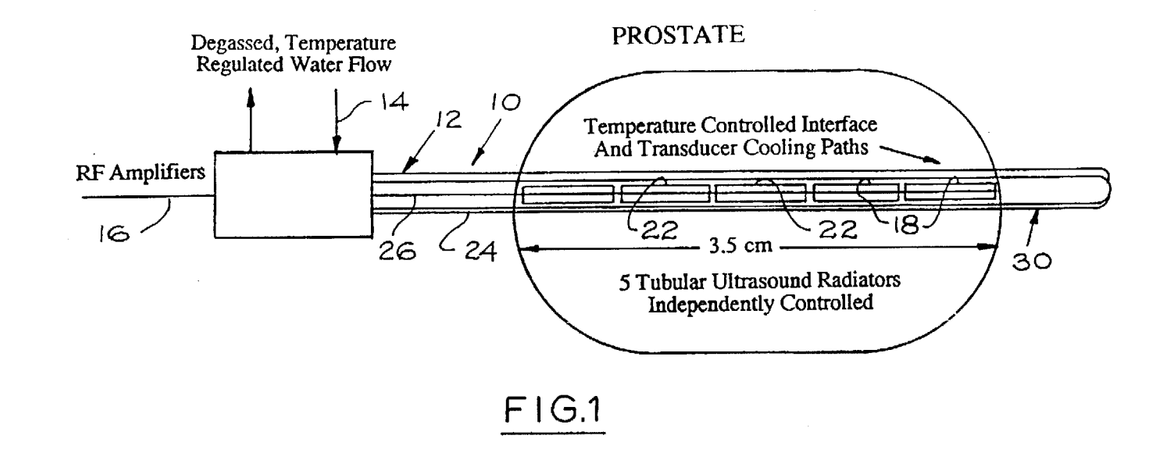
FIG. 1 illustrates a schematic view of a thermotherapy device constructed in accordance with one form of the invention.

Referring now to the figures and more particularly to FIG. 1, a thermotherapy device constructed in accordance with the invention is indicated generally at 10. Throughout the application when referring to "thermotherapy," this terminology shall be meant to include both thermotherapy treatment as well as hyperthermia treatment unless specifically stated to exclude one therapy.

The thermotherapy device includes a delivery system 12 which is coupled to the degassed and temperature regulated water flow 14 as well as RF amplifiers 16 and more fully described in U.S. patent application Ser. No. 08/083,967. While five tubular ultrasound transducers 18 are shown for non-limiting, illustrative purposes, it will be apparent to one skilled in the art that the number and configuration of ultrasound transducers can be varied depending on the particular application involved.

The delivery system can take a number of forms, though preferably a delivery system such as the one described in U.S. patent application Ser. No. 07/976,232 is used. The critical parameters of the delivery system 12 include the ability to provide degassed and temperature related water flow into the delivery system adjacent prostate tissue to be treated, as well as enabling individual control of each of the ultrasound transducers 18.

The ultrasound transducers 18 are preferably substantially cylindrical in shape. Conventional transducers 18 having this shape radiate a substantially symmetrical energy field. This has been found to be undesirable in prostate treatment as explained in detail in U.S. patent application Ser. No.

08/083,967. As described therein, the primary problem with a symmetrical energy field is heating of the rectal wall during prostate treatment. Irreversible damage to the rectal wall can result from such an energy field if power levels are sufficient to effectively treat areas of the prostate. Accordingly, the ultrasound transducers 18 are modified in accordance with one form of the invention.

Figure 2:
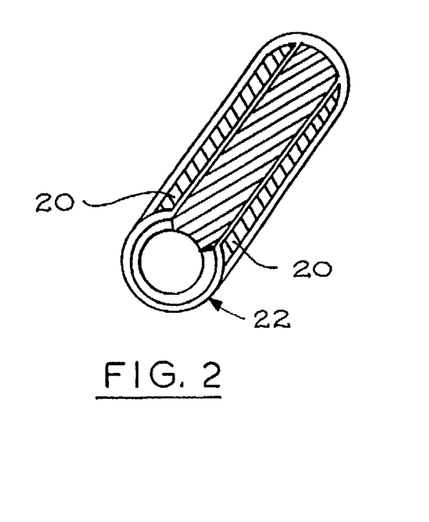
FIG. 2 shows an isometric view of an ultrasound crystal having a portion of its electrode coating removed.
Figures 3, 4:
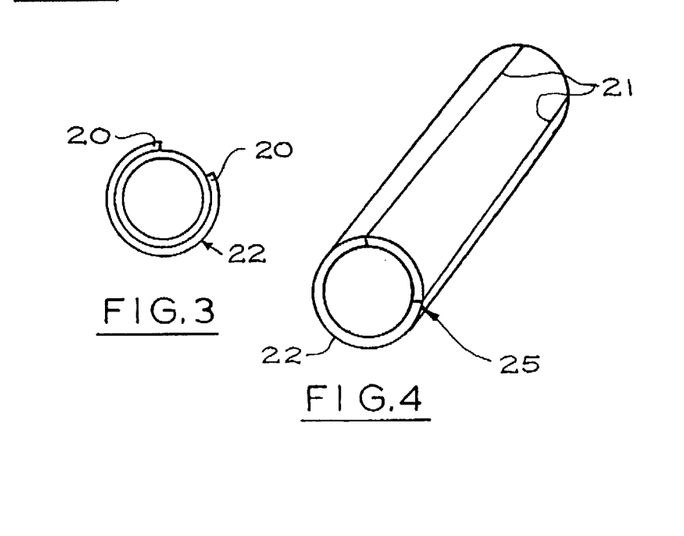
FIG. 3 illustrates an end view of the ultrasound crystal constructed in accordance with the invention and shown in FIG. 2.
FIG. 4 shows an isometric view of an ultrasound crystal including two score lines creating a region rendered incapable of radiating ultrasound energy.

The ultrasound transducers 18 are modified to create a portion incapable of producing virtually any ultrasound energy. This can be accomplished in one of two ways in accordance with this form of the invention. The first method (as shown in FIGS. 2 and 3) involves removing the electrode coating 20 from a portion of the ultrasound crystal 22. As used herein, the term "ultrasound crystal" shall refer to the nickel-plated piezo ceramic structure which is unconnected to a housing 24, power leads 26 or the RF amplifiers 16. The term "ultrasound transducer" shall refer to the ultrasound crystal 22 coupled to power leads 26 and mounted on a housing 24. Removing part of the electrode coating 20 as shown in FIGS. 2 and 3 provides a means for protecting the rectal wall of the patient from undesirable heating by shaping the energy field. This enables energy levels, and therefore the heating temperatures of the prostate, to be increased for more effective thermal therapy.

An alternative way of producing a portion which is substantially incapable of producing ultrasound energy is to score the electrode portion 21 of the ultrasound crystal 22. While the depth of the score lines 28 can be varied, preferably the scoring extends to a depth of 40–50% of the depth of the ultrasound crystal 22 exterior. The scoring can be accomplished using conventional cutting tools such as a diamond saw.

While a variety of ultrasound transducer housings 24 and delivery systems 12 can be used, preferably a delivery system 12 produced by Dornier Medical Systems, Inc. and sold commercially is used. The delivery system 12 can be reamed out to fit the size of ultrasound transducer housing assembly 30 as desired.

Figure 14:
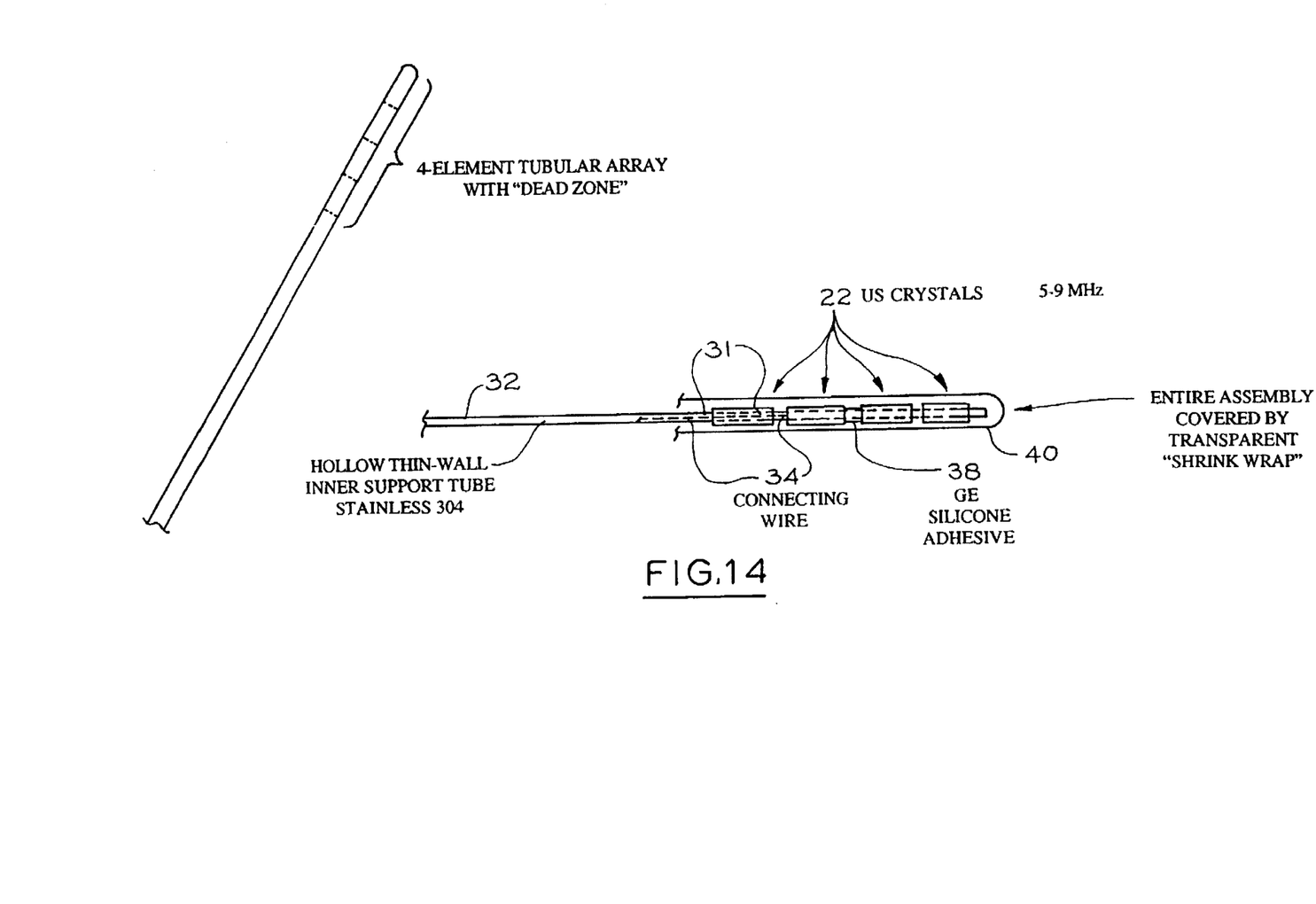
FIG. 14 shows a front view of an ultrasound applicator constructed in accordance with one form of the invention.

The ultrasound transducer housing assembly 30 can comprise a wide variety of configurations. Preferably, the assembly 30 is produced by producing apertures 31 in a thin walled tube 32, through which the power leads 34 for the ultrasound crystal 22 are run as shown in FIG. 14. The thin walled tube 32 can comprise a variety of biocompatible, noncorrosive materials, although preferably No. 304 stainless steel (thin needle stock) is used. The wires are run through the apertures 31, and an ultrasound crystal 22 is slid over the power leads 34, and soldered thereto. Any number of crystals 22 can be mounted this way, depending on the length of the thin wall tube 32 and the application desired. Next, silicone sealant 38 such as that sold commercially by General Electric as Silicon II Glue Seal and Gasket is deposited between the ultrasound crystals 22 and over the thin walled tube 32. The silicone sealant 38 acts as an adhesive, but allows the vibration necessary for efficient ultrasound energy radiation. The silicone sealant 38 also provides a water tight seal. While the assembly could be used in this form, preferably the assembly 30 is covered with shrink-wrap material 40 such as "SPIROBOUND" heat-shrink tubing which shrinks when exposed to heat. The shrink-wrap is exposed to a conventional heat source such as a propane torch in a controlled manner, and one obtains even shrinkage and a good seal by technique such as rotating the assembly 30 while heating. The resulting assembly is robust and highly efficient.

Figure 15A:
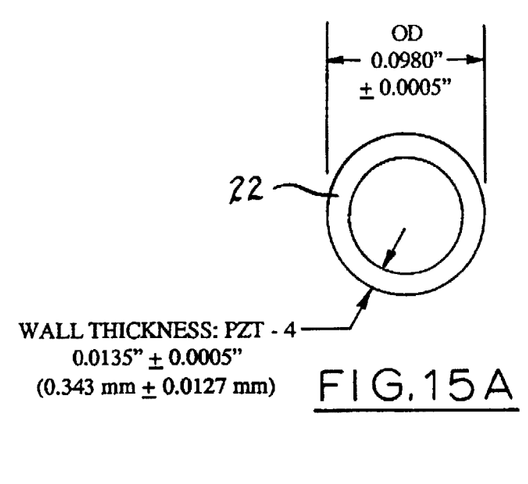
FIG. 15A illustrates an end view of an ultrasound crystal useful in one form of the invention.
Figure 15B:
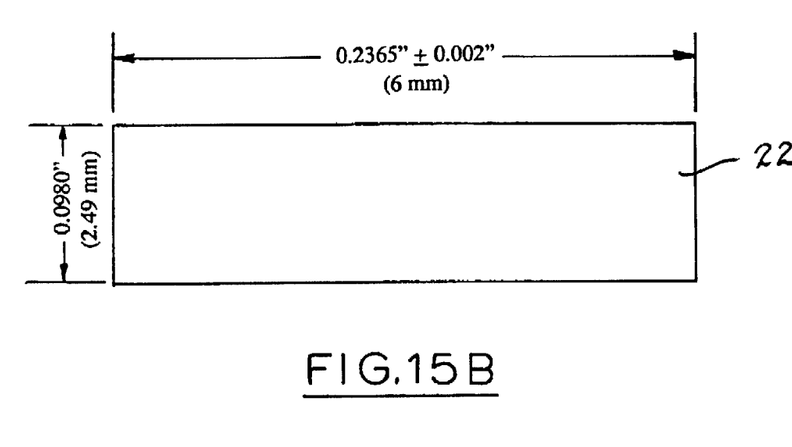
FIG. 15B shows a front view of the crystal shown in FIG. 15A.

While a variety of ultrasound crystals 22 can be used, preferably the ultrasound crystal 22 shown in FIGS. 15A and 15B is used. For additional transducer details, please see FIGS. 14A and 14B. This ultrasound crystal 22 is preferably provided by Stavely Sensors, Inc. of East Hartford, Conn. or Valpey-Fischer Corp. of Hopkinton, Mass., and produces extremely high power output for such a small sized transducer.

EXAMPLE

In accordance with this form of the invention, a transurethral multielement ultrasound applicator was used as a means of improving heating penetration, spatial localization, and dynamic control to afford better treatments for cancer and BPH. This structure provided longitudinal control of heating to cover the anterior-lateral portion of the prostate while sparing the region around the rectum and verumontanum. Computer simulations, acoustic measurements, and in vivo thermal dosimetry studies confirmed the usefulness of this form of the invention.

For a nonlimiting, illustrative example, prototype applicators were fabricated with four tubular transducer elements (each 6 mm long, 2.5 mm OD) attached to form a segmented array. Separation between elements was approximately 0.5 mm. Each transducer was modified to produce uniform coverage of the anterior and lateral portions of the prostate and to ensure that no acoustic energy would be delivered to the rectum during clinical use. The multielement applicator was designed to be inserted within a modified catheter delivery system previously developed for microwave BPH therapy (Dornier Medical Systems, Inc.), with annular counter-current flow for water coupling of the acoustic energy and temperature regulation of the catheter/urethra interface. (The cooling provided by the delivery system protects the urethra).

The heating performance of these ultrasound applicators was evaluated using computer simulation programs to calculate the acoustic fields and corresponding thermal distributions in tissue. The power deposition ($<q>$) of these cylindrical sources in tissue can be approximated by the following expression:

$$<q> = \frac{2\alpha I_o f r_o}{r} e^{-2\alpha(r-r_o)} \qquad (1)$$

where $I_o$ is the intensity at the transducer surface, $r_o$ is the radius of the transducer, r is the radial distance from the center of the transducer, $\alpha$ is the amplitude attenuation coefficient, and f is the frequence (MHz).

The temperature distributions resulting from the compiled power disposition patterns were calculated using the bio-heat transfer equation (BHTE), a descriptive model of tissue thermal characteristics:

$$\nabla 2(kT) - \omega_b c_b (T-T_a) + <q> = 0, \qquad (2)$$

where k is the tissue thermal conductivity, $\omega$ is the blood perfusion rate, $c_b$ is the specific heat of tissue, T is the tissue temperature and $T_a$ is the arterial blood temperature. The steady-state solution to this equation was computed using the finite difference technique with successive over-relaxation. Typical values used were: $\alpha=5$ Np m$^{-1}$ MHz$^{-1}$, k=0.528 W m$^{-1}$ °C.$^{-1}$, $\omega$=1–10 kg m$^{-3}$ s$^{-1}$, c=3680 J kg$^{-1}$ °C.$^{-1}$, p=1000 kg m$^{-3}$. A perfusion of $\omega$=2.0 kg m$^{-3}$ s$^{-1}$ represents a moderately perfused tissue (resting muscle); most tumors range from 0.1–5.0 kg m$^{-3}$ s$^{-1}$. These simulations were configured to accurately model the presence of applicator water cooling of the applicator/tissue interface. The acoustic force-balance technique adapted for cylindrical radiators was used to measure the acoustic output power from these tubular transducers as a function of drive frequence and applied electrical power.

Figure 5:
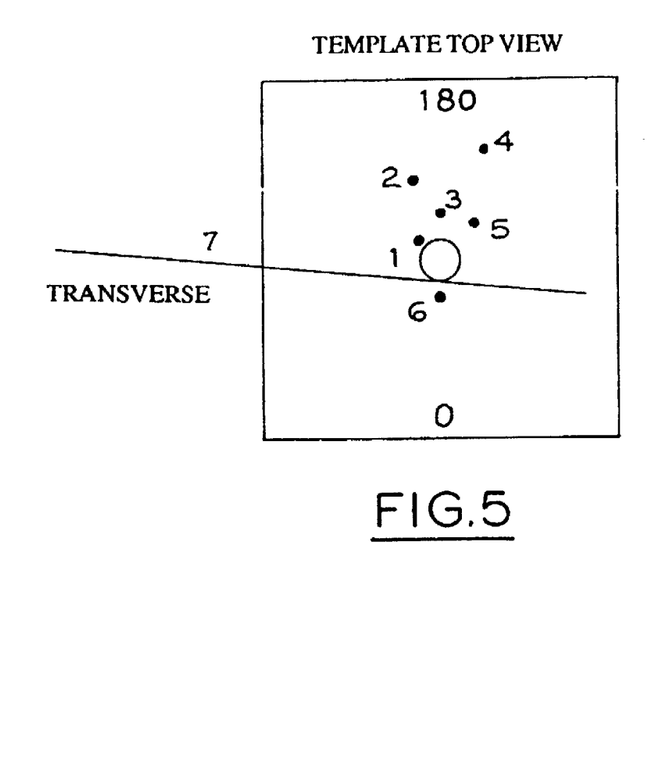
FIG. 5 shows a top view of the template implant for in vivo thermometry placement with respect to the applicator for thermal dosimetry measurements.
Figure 6:
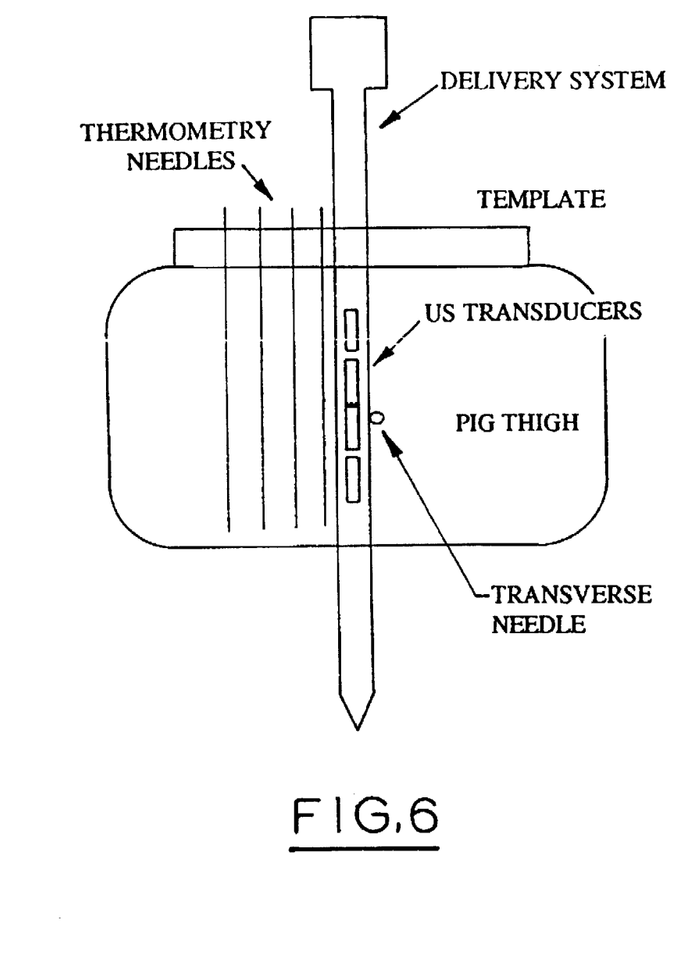
FIG. 6 illustrates a front view of the template implant for in vivo thermometry placement with respect to the applicator for thermal dosimetry measurements.

A 100 lb female farm pig was anesthetized using 1.5% Isoflourane and 0.6 l/min O2. A 0.5 inch thick Plexiglas template was used to ensure alignment of the thermometry probe tracks with the catheter delivery system (see FIGS. 5 and 6 for set up). 20 g. needles were inserted through the template for thermometry tracks at radial distances of 0.5 to 3.0 cm from the catheter wall but aligned with the axis of the delivery system. A tangential thermometry track was inserted orthogonal to the axis of the delivery system, 5 cm deep within the thigh, and glancing the surface of the catheter delivery system. Multijunction thermocouple probes were inserted within the needles and moved in 0.5 cm increments to obtain temperature maps along the length of the applicator. The approximate radial depth of sensed needles from the outer surface of the delivery catheter was 0.5, 1.0, 2.0 and 3.0 cm.

A multichannel RF amplifier system was used to power each transducer within the applicator. The frequency sweep on center frequency for each transducer was adjusted to produce a uniform pressure disturbance as visualized on the surface of water. A flow rate of 220 ml/min of 35° C. degassed water was maintained to the delivery system for the duration of the experiment.

The applicator was aligned within the catheter so that the "dead zone" aimed at #6 (probe track 6) and the central heating zone was aimed at #3. 2 watts of RF power was applied to each transducer element of the applicator until a pseudo steady-state was achieved after 5 minutes. Temperature maps were obtained for all thermometry probes, and then the power was turned off. The applicator was then rotated counter clockwise by 30° within the delivery system. After the tissue cooled back to equilibrium (10–20 min) the process was repeated. This sequence was repeated until the pseudo-steady-state temperature profiles were measured for each thermometry tract as the applicator was rotated in 30° increments for a total of 180°.

Figure 7:
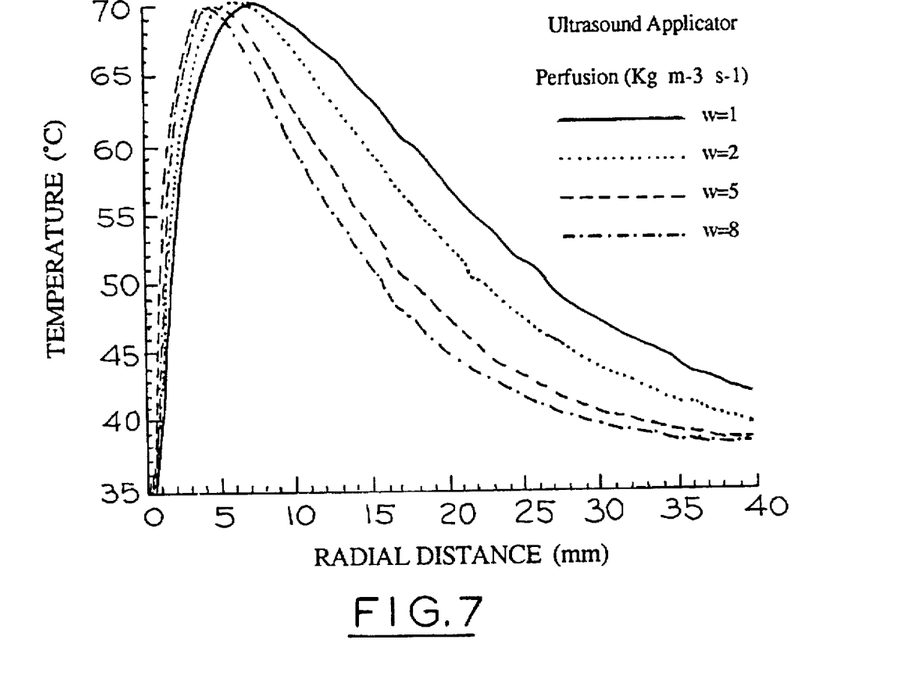
FIG. 7 illustrates simulated temperature profiles from a 2.5 mm diameter ultrasound applicator within a 6 mm diameter water-cooled delivery catheter with $T_c$ equal to 20° C.

Simulated radial temperature profiles (see FIG. 7) illustrated that effective heating is possible to 2 cm depth with concurrent cooling to protect the urethral mucosa ($T_c=20°$ C., 7 MHz ultrasound). These experimental results (see FIG. 9) demonstrate the distinct advantage of multielement ultrasound applicators over other techniques: the power deposition along the applicator length can be adjusted to produce more desirable (elongated) temperature distributions such as adjusting heating length and accommodating dynamic changes in blood perfusion and tissue heterogeneity.

Figure 8:
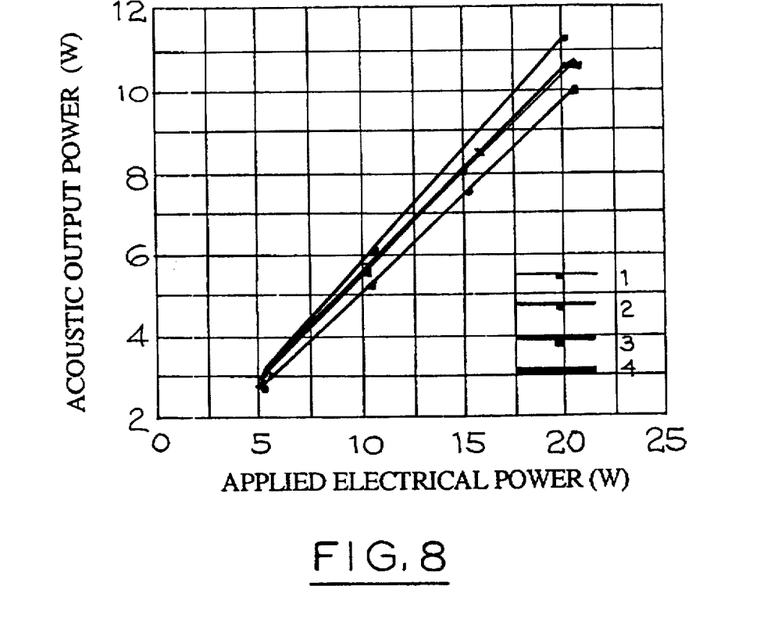
FIG. 8 illustrates acoustic output power levels as a function of electrical input power for four individual tubular array transducers driven at peak resonant frequency.
Figure 9A:
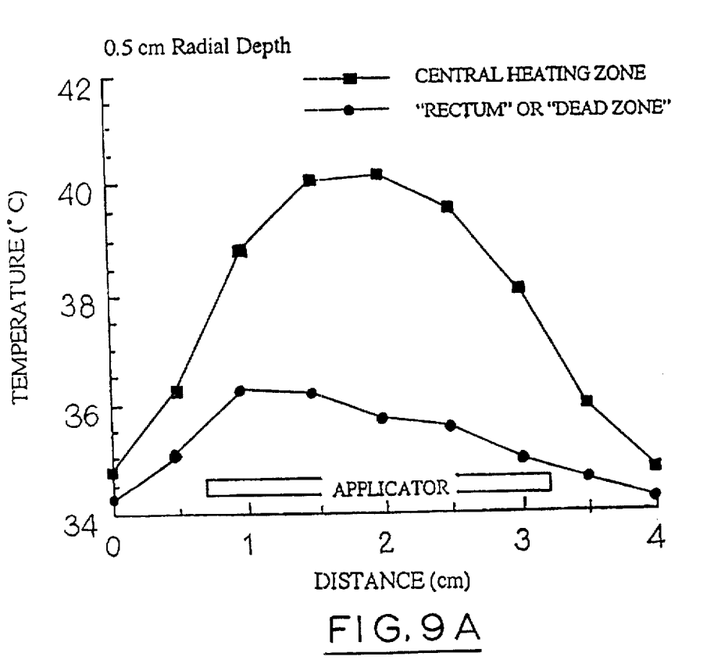
FIGS. 9A–9D show longitudinal temperature profiles measured in pig thigh muscle at A) 0.5 cm; B) 1 cm; C) 2.0 cm; and D) 3.0 cm radial depths.
Figure 9B:
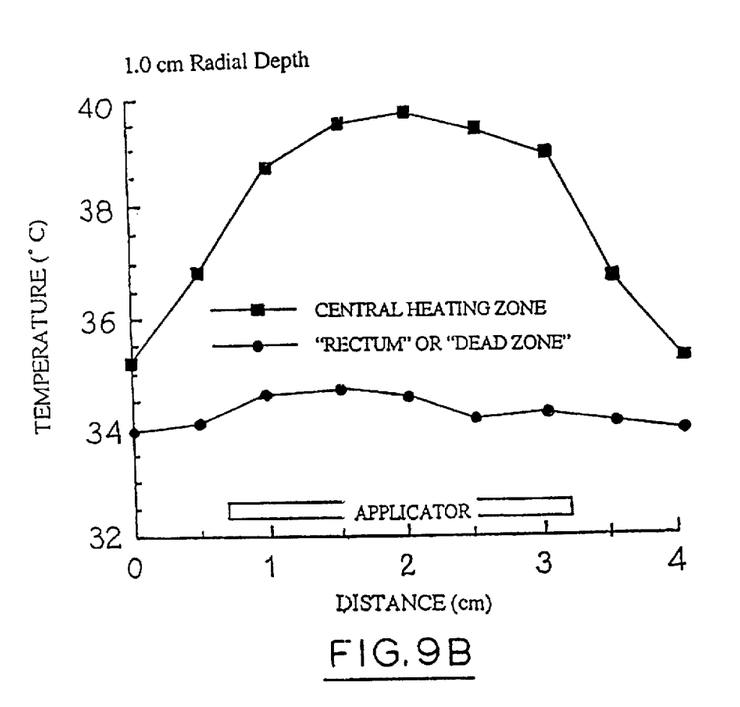
Figure 9C:
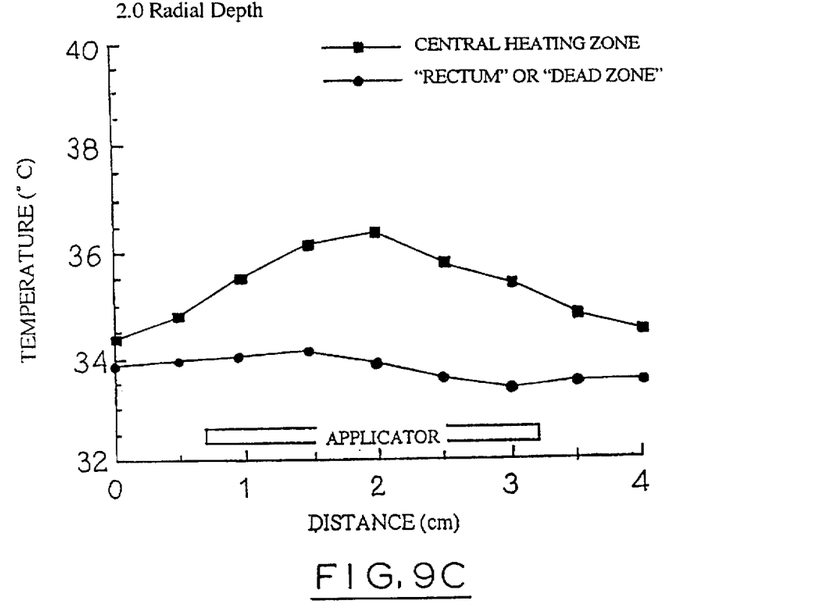
Figure 9D:
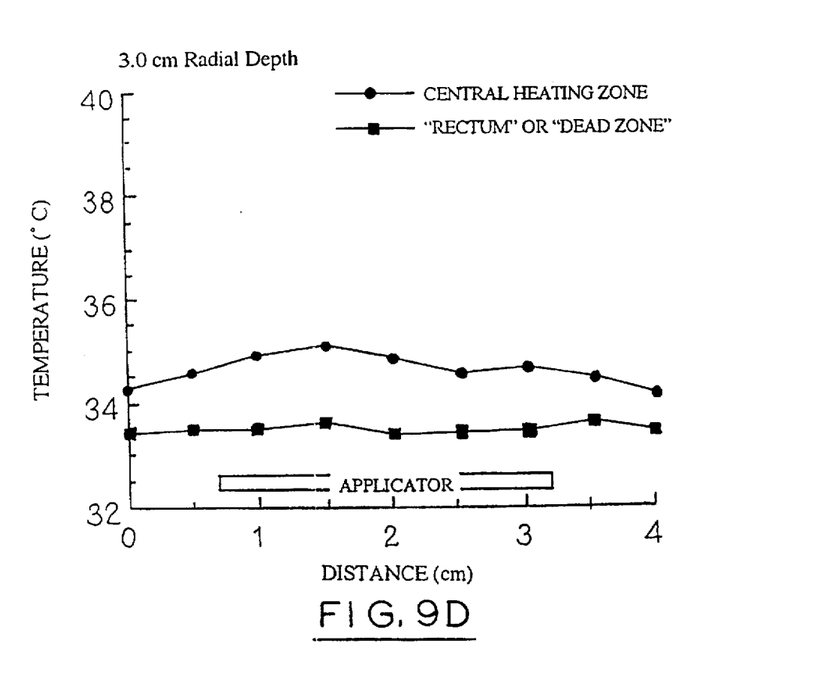

The acoustic efficiencies of these cylindrical ultrasound transducers was between 55–60% at the peak resonant frequency. These efficiencies are high for such very small crystals. FIG. 8 demonstrates that acoustic power levels of almost 12 w per transducer are attainable with this applicator design.

Figure 10:
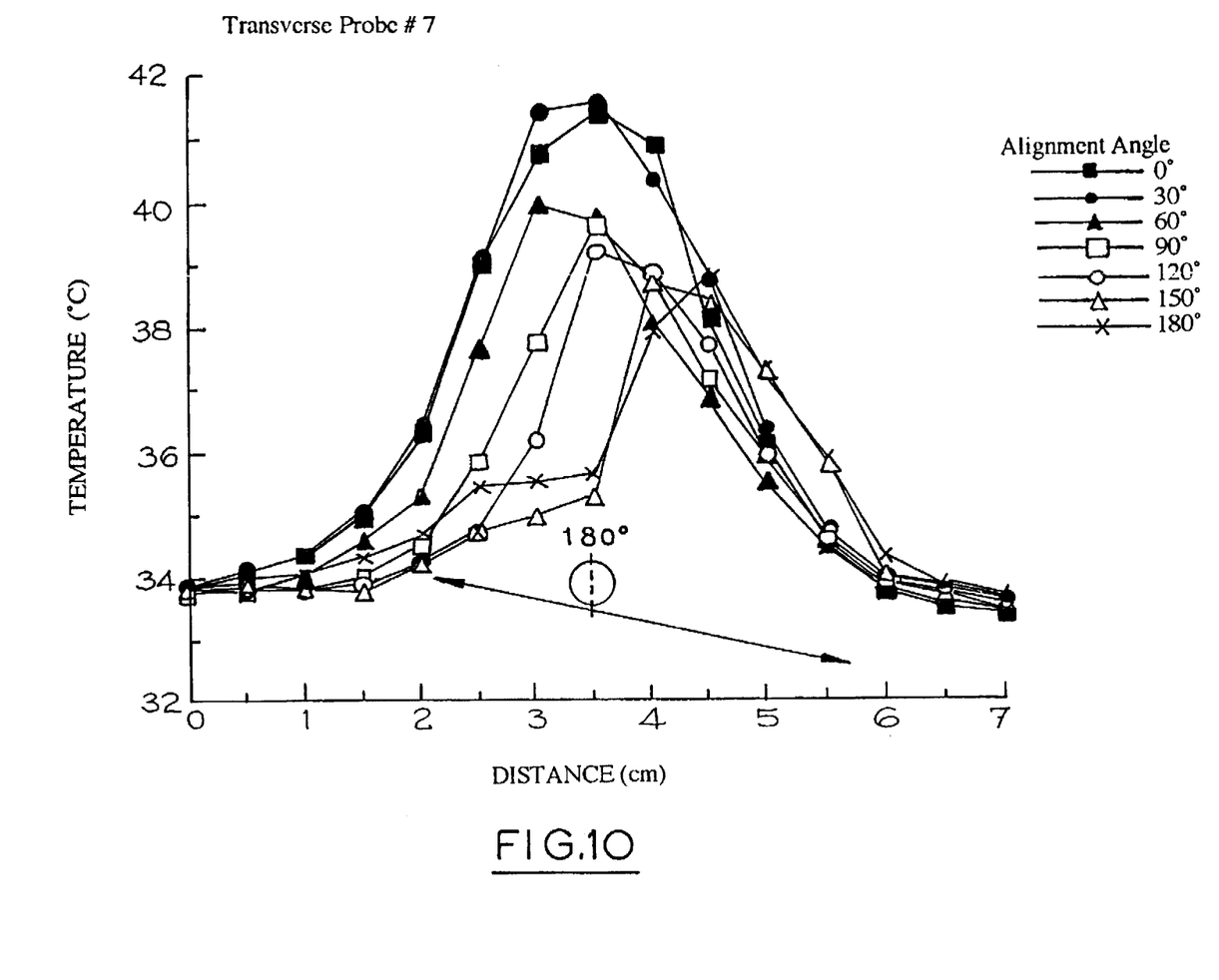
FIG. 10 illustrates tangential temperature profiles measured in the pig thigh muscle across the central heating zone.
Figure 11A:
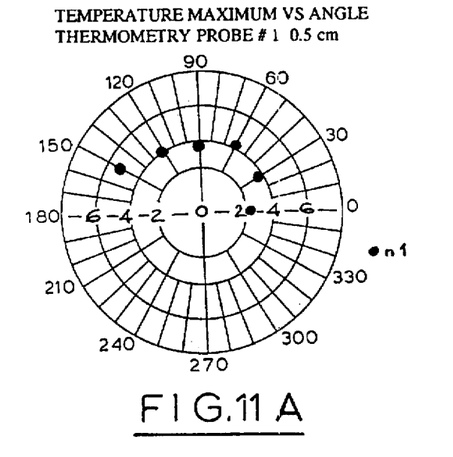
FIGS. 11A–11E illustrate angular temperature profiles at a) Probe #1, 0.5 cm depth; b) Probe #2, 2 cm depth; c) Probe #3, 1.0 cm; d) Probe #4, 3.0 cm and e) Probe #5, 1.0 cm.
Figure 11B:
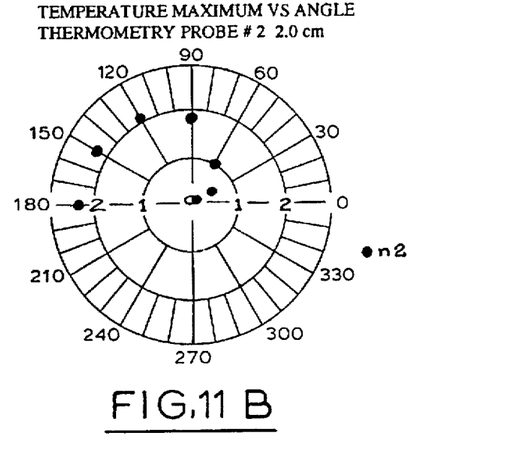
Figure 11C:
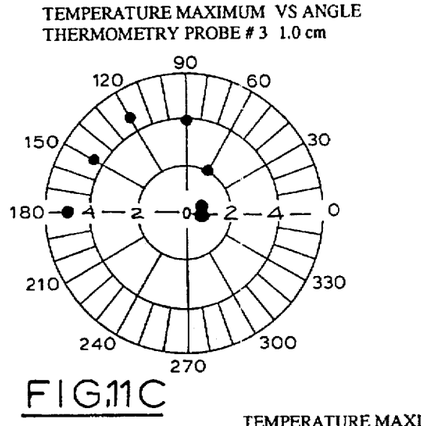
Figure 11D:
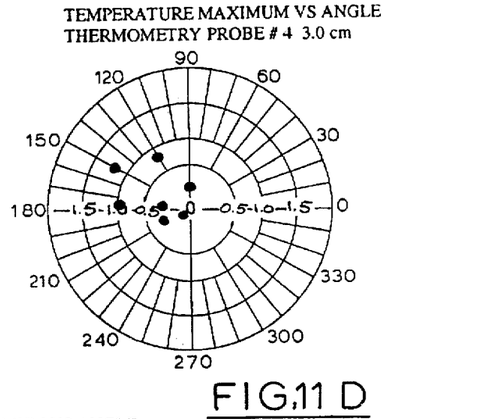
Figure 11E:
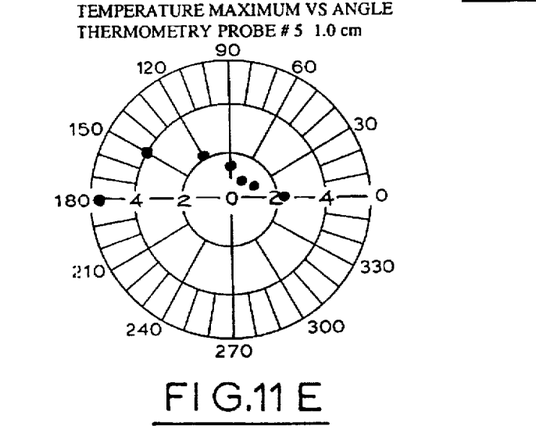
Figure 12A:
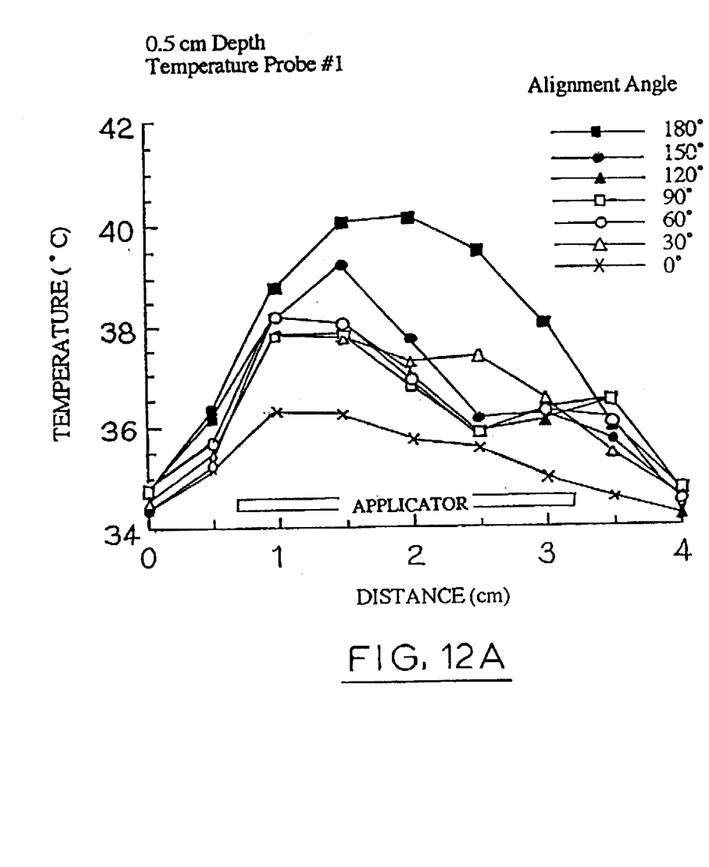
FIGS. 12A–12E show a different plot format of angular temperature at a) Probe #1, 0.5 cm depth; b) Probe #2, 2 cm depth; c) Probe #3, 1.0 cm; d) Probe #4, 3.0 cm and e) Probe #5, 1.0 cm.
Figure 12B:
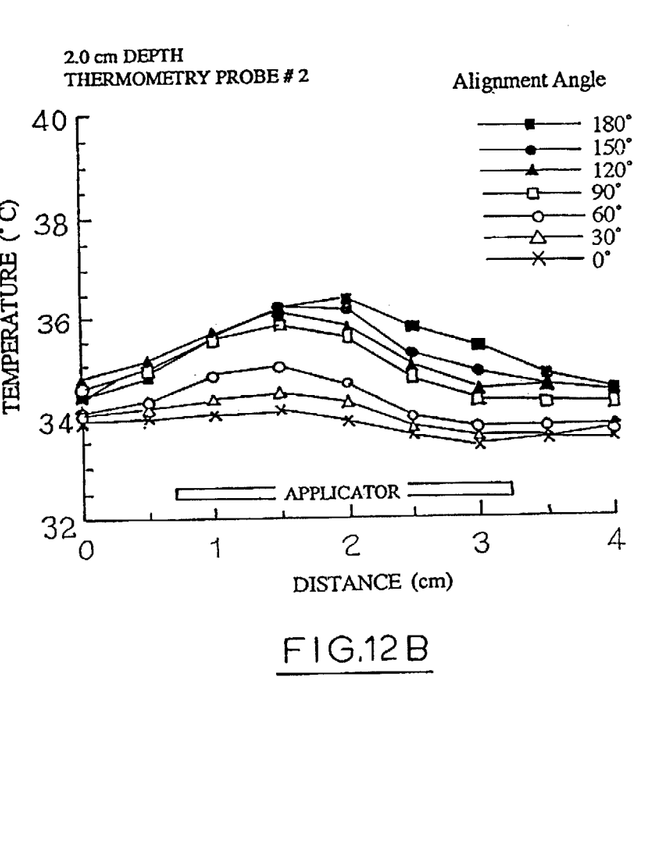
Figure 12C:
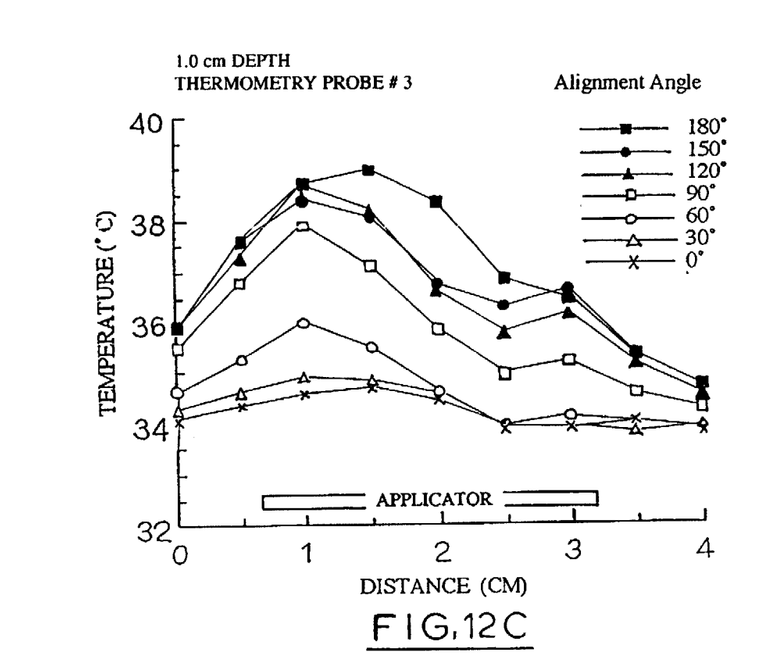
Figure 12D:
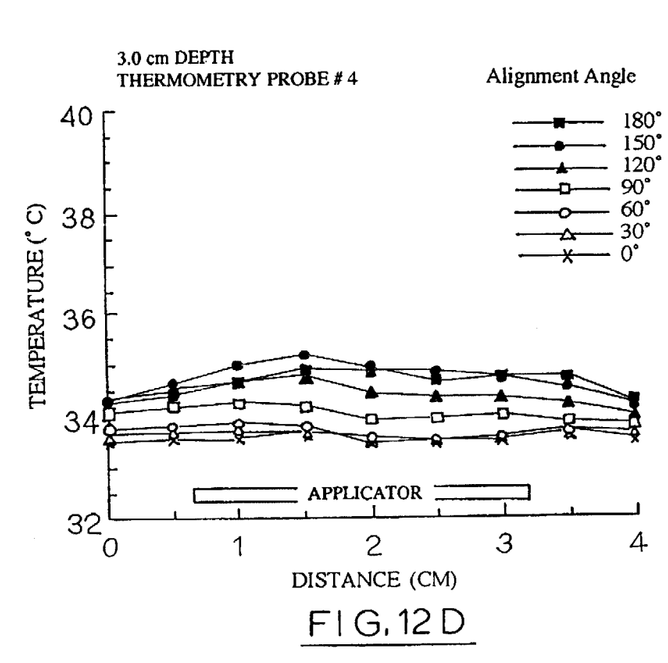
Figure 12E:
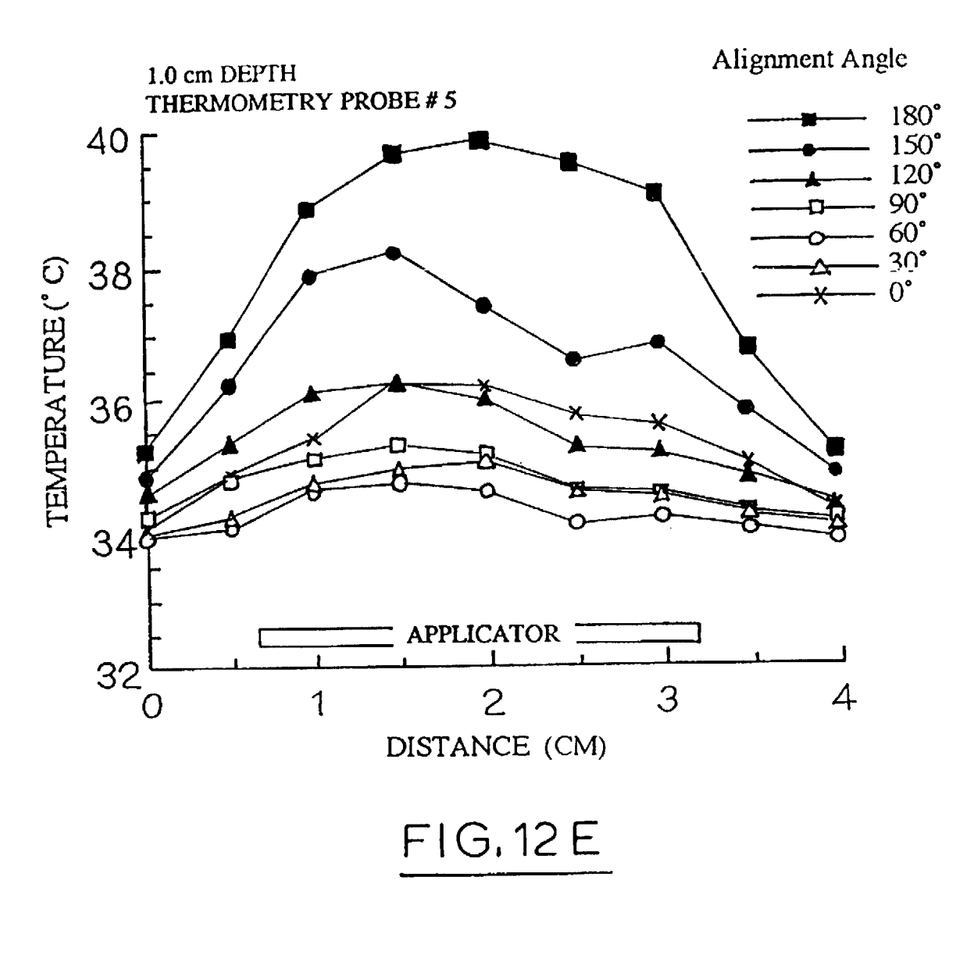
Figure 13A:
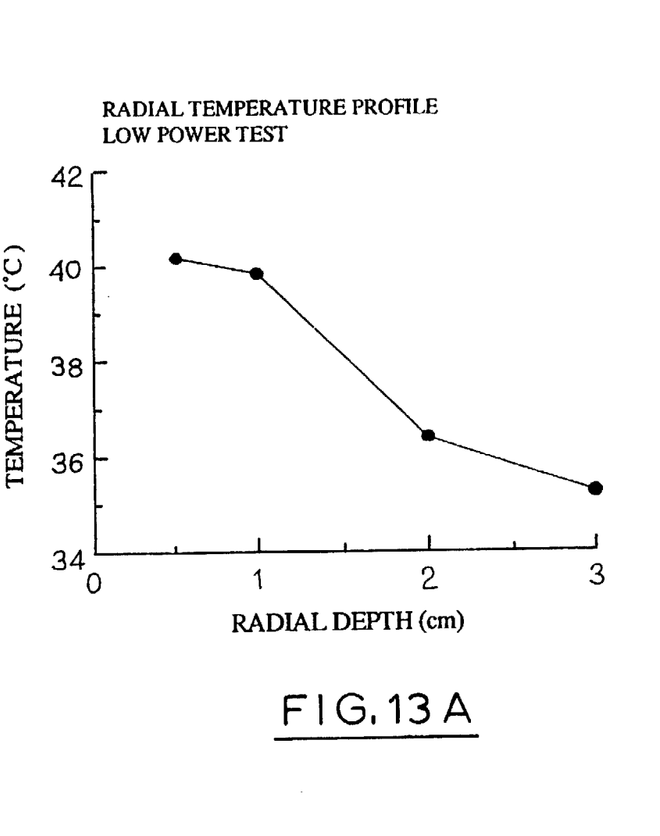
FIGS. 13A–13D illustrate radial temperature profiles in the pig thigh muscle after ten minutes of therapy for low power tests (FIGS. 13A and 13C) and high power tests (FIGS. 13B and 13D)
Figure 13B:
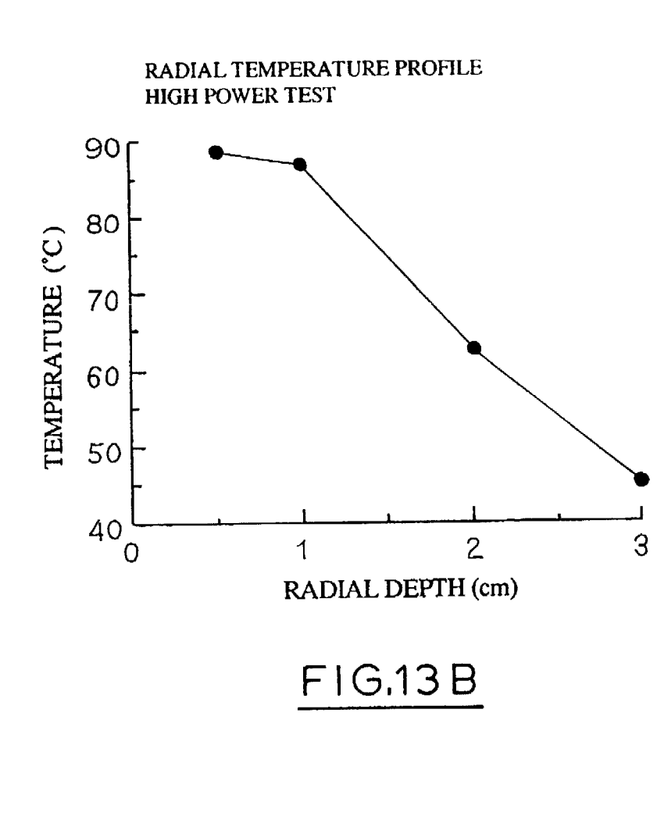
Figure 13C:
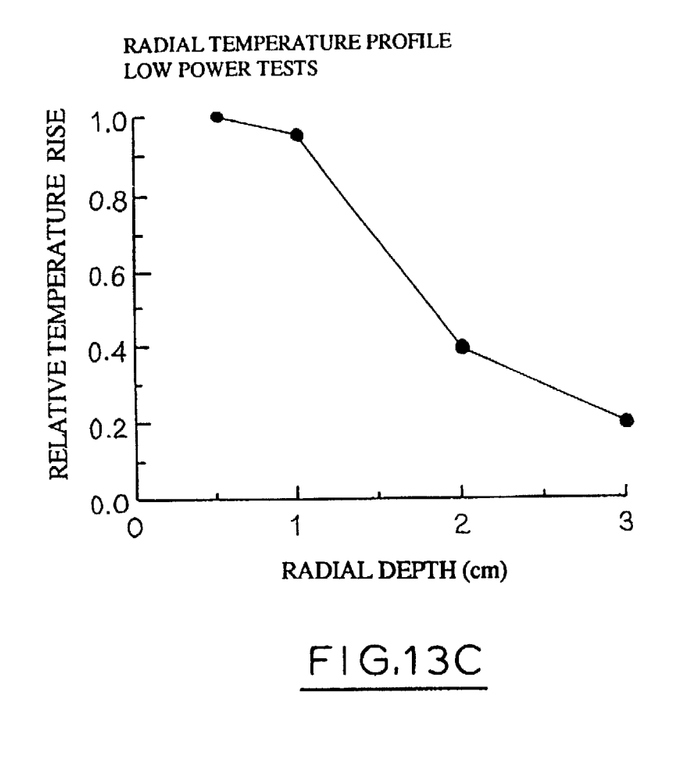
Figure 13D:
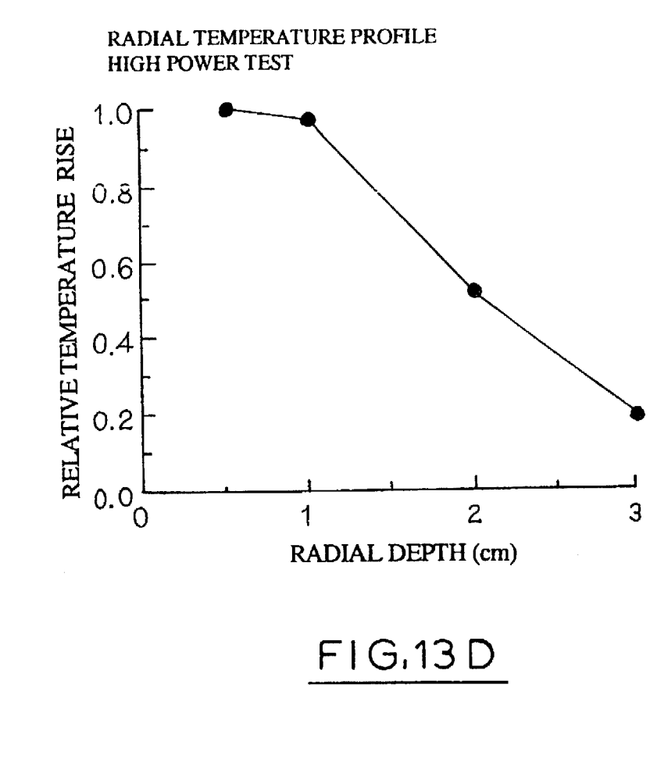

The temperature distributions produced by this applicator in pig thigh muscle were measured using low temperature repetitive heating trials. (This was necessary to ensure repeatability between heating sessions and to avoid thermal damage to the tissue). The longitudinal temperature profiles at varying radial depths from the applicator surface are shown in FIGS. 9A–E, demonstrating that within the central heating zone the therapeutic region extends towards the ends of the applicator and is fairly uniform, while isolated from the "rectal" region. The tangential profiles (FIG. 10) measured across the central heating zone illustrate a radial extension of the heated region of 2-3 cm diameter. From a series of measurements at different rotational angles, the steady-state peak (longitudinal) temperature rise as a function of applicator rotational angle at varying depths are shown in FIGS. 11A–E, illustrating the preferential localization of the heating to the anterior and lateral regions while protecting the rectum (located at zero degrees on the plots). Further data relating to temperature rise as a function of alignment angle and longitudinal distance along the application are plotted in FIGS. 12A–E.

Finally, the applicator was repositioned to the initial startup orientation, and 8–10 acoustic watts of power was applied to each transducer in order to thermally ablate the "target" region and pseudo steady state temperatures were obtained. The radial temperature distribution achieved during the ablative sequence is shown in FIG. 12.

These results verified the usefulness of using the transurethral ultrasound applicator of present invention for thermal therapy of the prostate. These applicators, inserted within a water-cooled delivery-catheter, can produce heated regions extending more than 2 cm in radial depth, while sparing the urethral mucosa. A significant advantage of multi-transducer ultrasound applicators is that the longitudinal power deposition (heating pattern) can be dynamically altered in response to tissue heterogeneities, thermally induced changes in blood perfusion, and to tailor the size of the treated region. In addition, the beam distributions from these applicators can be shaped in order to produce desired circumferential or angular heating patterns which can protect the rectal mucosa while localizing the energy deposition to the anterior and lateral sections. This is a significant improvement over previous designs using single antenna microwave energy sources, which produce more elliptical or "football shaped" distributions which can not be adjusted. The in vivo thermal dosimetry experiments also show that therapeutic temperatures in excess of 80° C. can be obtained with the present invention.

While preferred embodiments have been illustrated and described, it should be understood that changes and modifications can be made therein without departing from the invention in its broader aspects. Various features of the invention are defined in the following claims.

What is claimed is:

1. An apparatus for applying thermal therapy to a prostate gland, comprising:

a support tube having a longitudinal central passageway;

a power lead for providing power and said power lead channeled through said longitudinal central passageway;

an ultrasound crystal disposed around at least part of said support tube and said ultrasound crystal coupled to said power lead which provides the power to energize said ultrasound crystal and generate ultrasound energy providing thermal therapy to the prostate gland, said ultrasound crystal further including means for inactivating selected portions of said ultrasound crystal for reducing ultrasound energy directed to the rectal wall of the patient; and a sealant disposed in contact with said ultrasound crystal allowing vibration necessary for efficient ultrasound energy radiation for the thermal therapy to the prostate gland.

2. The apparatus as defined in claim 1 further including an outer covering disposed over said support tube, said outer covering comprising a shrink wrap material.

3. The apparatus as defined in claim 1 wherein said ultrasound crystal comprises a cylindrical shape concentrically disposed about said support tube.

* * * * *